United States Patent [19]

Gjerde

[11] Patent Number: 5,393,673

[45] Date of Patent: Feb. 28, 1995

[54] METHOD FOR PARTICULATE REAGENT SAMPLE TREATMENT

[75] Inventor: Douglas T. Gjerde, Saratoga, Calif.; Daniel R. Wiederin, Omaha, Neb.

[73] Assignees: Sarasep, Inc., Santa Clara, Calif.; Cetac Technologies Inc., Omaha, Nebr.

[21] Appl. No.: 252,046

[22] Filed: May 31, 1994

Related U.S. Application Data

[63] Continuation of Ser. No. 968,799, Oct. 30, 1992, abandoned.

[51] Int. Cl.$^6$ .......................... G01N 21/62
[52] U.S. Cl. .................. 436/171; 436/149; 436/154; 436/173; 436/174; 436/178
[58] Field of Search ............. 436/154, 149, 151, 153, 436/164, 161, 168, 169, 171, 172, 174, 175, 176, 178, 173; 422/54

[56] References Cited

U.S. PATENT DOCUMENTS

| | | | |
|---|---|---|---|
| 2,563,006 | 8/1951 | Collier | 127/46.2 |
| 3,224,358 | 12/1965 | Spielvogel | 99/278 |
| 3,586,294 | 6/1971 | Strong | 366/165 |
| 3,883,312 | 5/1975 | Youngman | 422/212 |
| 4,097,338 | 6/1978 | Konttinen et al. | 435/26 |
| 4,357,143 | 11/1982 | Scott | 204/153.1 |
| 4,414,325 | 11/1983 | Masuda et al. | 435/7.4 |
| 4,432,893 | 2/1984 | Lee et al. | 588/118 |
| 4,451,434 | 5/1984 | Hart | 422/102 |
| 4,458,014 | 7/1984 | Ebersole | 435/74.32 |
| 4,481,134 | 11/1984 | Angelini et al. | 588/19 |
| 4,503,143 | 3/1985 | Gerber et al. | 435/7 |
| 4,525,713 | 6/1985 | Barletta et al. | 340/825.54 |
| 4,526,713 | 7/1985 | Chino et al. | 252/632 |
| 4,550,019 | 10/1985 | Polson | 436/539 |
| 4,588,680 | 5/1986 | Bucher et al. | 435/5 |
| 4,636,335 | 1/1987 | Kawamura et al. | 252/629 |
| 4,650,770 | 3/1987 | Liu et al. | 436/537 |
| 4,652,533 | 3/1987 | Jolley | 436/172 |
| 4,665,020 | 5/1987 | Saunders | 435/7 |
| 4,700,637 | 10/1987 | McCartney | 110/237 |

(List continued on next page.)

FOREIGN PATENT DOCUMENTS

| | | |
|---|---|---|
| 1103137 | 6/1981 | Canada . |
| 1294933 | 2/1986 | Germany . |
| 59-171863 | 9/1984 | Japan . |
| 62-002163 | 1/1987 | Japan . |
| 62-093663 | 4/1987 | Japan . |
| 62/093664 | 4/1987 | Japan . |

OTHER PUBLICATIONS

Zhur. Anal. Khim, (1966), 21:1217-1222, Yu et al (Reference Not Available At This Time).

R&D Magazine, (1992), P. 132 (Reference Not Available At This Time).

Analytical Proceedings, (1989) 26:382:384, "Plasma-Atomic Fluorescence Spectrometry", Greenfield et al.

Applied Spectroscopy, (1989) 43:1132-1135, "Preconcentration Of Trace Elements In Aluminum Alloys Using a Chelating Ion-Exchanger And Determination by ICP-AES", Dumont et al.

Analytica Chimica Acta, (1985) 173:305-309, "Iminodiacetic Acid Ethylcellulose As a Chelating Ion Exchanger", Horvath et al.

Analytical Chemistry, (1986) 58:1352-1355, "Carboxymethylated Polyethylenimine-Polymethylene-Polyphenylene Isocyanate Chelating Ion Exchange Resin Preconcentration For Inductively Coupled Plasma Spectrometry", Horvath et al.

(List continued on next page.)

Primary Examiner—Donald E. Czaja
Assistant Examiner—Lien Tran
Attorney, Agent, or Firm—Oblon, Spivak, McClelland, Maier, Neustadt

[57] ABSTRACT

A method detecting the presence or concentration of an analyte in a sample is described in which the sample is mixed with a particulate reagent to form a stable flowable suspension prior to introduction of the sample into an analytical device or detector in order to eliminate memory effects. Preconcentration of the sample bound to the particulate reagent improves sensitivity of the analytical method.

30 Claims, 2 Drawing Sheets

U.S. PATENT DOCUMENTS

| | | | |
|---|---|---|---|
| 4,703,017 | 10/1987 | Campbell et al. | 436/501 |
| 4,780,423 | 10/1988 | Bluestein et al. | 436/527 |
| 4,793,947 | 12/1988 | Izumida et al. | 252/628 |
| 4,842,701 | 6/1989 | Smith et al. | 436/173 |
| 4,900,434 | 2/1990 | Schade | 210/189 |
| 4,978,506 | 12/1990 | Calderwood | 422/73 |
| 5,102,626 | 4/1992 | Beach | 436/171 |
| 5,149,661 | 9/1992 | Gjerde et al. | 436/178 |
| 5,198,368 | 3/1993 | Khalil et al. | 436/178 |

OTHER PUBLICATIONS

Applied Spectroscopy, (1988), 42:456–460, "A Detector For Liquid Chromatography And Flow Injection Analysis Using Surface-Enhanced Raman Spectroscopy", Freedman et al.

Science, (1992), 256:649–651, "Colloid Formation During Waste Form Reaction: Implications For Nuclear Waste Disposal", Bates et al.

S. Afr. J. Chem. (1984), 37:81–84, "Determination Of Traces of Noble Metals Adsorbed Onto An Ion-Exchange Resin By Its Direct Injection Into An ICP Source", Watson et al.

Environ. Sci. Technol. (1992) 26:1073.

METHOD FOR PARTICULATE REAGENT SAMPLE TREATMENT

This application is a continuation of application Ser. No. 07/968,799, filed on Oct. 30, 1992, now abandoned.

BACKGROUND OF THE INVENTION

1. Field of the Invention:

The present invention is directed to a method of detecting the presence or concentration of an analyte in a sample solution. More particularly, the invention is directed to a method of improving the sensitivity and substantially eliminating memory effects in analytical detection methods by premixing the sample solution with a particulate reagent such that the analyte is bound to the particulate reagent prior to analysis.

2. Discussion of the Background

Analytical methods are employed to analyze a wide variety of sample types. Often, the initial chemical or physical form of a sample is incompatible with the analytical method or instrument and so the sample must be changed or treated before analysis. For example, solid samples are often dissolved to form an aqueous solution prior to analysis. A number of other sample treatments are also used to enhance the analysis process, including treatments to concentrate analytes, reduce sample matrix interferences or to improved sample introduction ease or efficiency. Ideally, these treatments result in faster, more sensitive and more accurate analysis.

The sensitivity of an analytical method is of critical importance. A sample may contain analyte concentrations that are of interest, but are still lower than the detection limits of the system used to analyze them. Inadequate instrument sensitivity can be caused by lack of an adequate amount of analyte, by low analyte concentrations or by the presence of interfering substances. In these cases, the apparent sensitivity of the instrument can be improved by better methods of sample introduction, preconcentration or removal of interfering substances.

For example, the determination of trace metals at low levels in drinking water is a common analytical problem. Current instrumentation, e.g., flame atomic absorption spectrometry, may not obtain the desired sensitivity. A rapid on-line continuous preconcentration method would allow the desired detection with improved sensitivity while maintaining high sample throughout.

Preconcentration of a sample may be accomplished by partial evaporation of the solvent. However, evaporation methods are not on-line methods and are generally extremely slow. Furthermore, evaporation is not selective. All materials that are not volatile are concentrated, whether these materials are of interest or not. Volatile materials are lost, whether they are of interest or not.

Numerous sample treatment and preconcentration methods are known, where the sample is passed through a packed bed of material in a column. The column may retain an interfering substance and let the analyte pass through the column to be analyzed, or alternatively, the column may retain and preconcentrate the analyte and let the sample matrix pass through the column to waste. See for example U.S. Pat. No. 4,357,143.

In a typical column application, transition metal ions are passed through a column containing a chelating ion-exchange resin. Analyte species are bound to the column while solvent and unwanted matrix components such as sodium ions pass through the column as waste. The column bound transition metal are then released from the column packing resin and washed from the column using an eluant. The eluting liquid usually has a different pH or polarity than the sample so that the analyte is released from the packing resin. Eventually, the analyte is transported to an instrument for analysis. Column preconcentration and matrix removal methods are subject to several limitations including reversible complexation effects, poor kinetic effects, increased analysis time and contamination.

To perform a preconcentration process using a column, the solid particles which chemically bind the analyte, e.g., by ion exchange, chelation, adsorption, etc., must be able to release the analyte species prior to analysis. Thus, packing resins which appear to be most suited to perform the preconcentration process because they bind the analyte of interest strongly and selectively, may not be useful because it is difficult or impossible to release the analyte from the column resin with a reasonable volume of eluant. Additionally, incomplete elution of analytes can cause memory effect problems.

Fast kinetics are desirable for column preconcentration operations. The best kinetics occur on the surface of the column packing material. Therefore, large surface area to volume ratios, i.e., small particles, are desirable for the column packing material. However, small suspension particles cannot be packed easily into a column without causing high fluid back pressures. Thus, the use of optimal particle sizes for binding analytes are not possible using preconcentration columns.

A preconcentration column must be loaded with sample and then the sample must be eluted from the column. This is a discontinuous process. Since the preconcentration column is usually used for many analyses, it must be cleaned and reconditioned between analyses. Accordingly, operation of a preconcentration/matrix removal column usually increases the analysis time.

The use of elution solvents introduces an additional step into the analysis process and may also introduce contamination into the sample eluted from the column. Furthermore, incomplete elution is one cause of memory effects. Residual material can elute causing a residual signal over a long period of time, i.e., a memory effect.

Another of the many problems which prevent accurate sensitive analytical analysis is the occurrence of memory effects. Memory effects are observed when residual analytes from a previous analysis are detected in a current analysis. More often, memory effects are observed from volatile elements that are adsorbed or retained through a variety of mechanisms within the components of an analytical device.

Memory effects are manifested in essentially two ways. First, the detected signal, from analyte trapped within the instrument and gradually released, may persist over a period of several minutes to several hours. This prolonged signal results in a high, changing background signal. As a result, the analysis of subsequent samples, especially those with low analyte concentrations, is difficult or impossible. A second manifestation of the memory effect is dependent upon the sample matrix. Some matrices may induce matrix-effected species to be retained within the analytical instrument. Other matrices may cause analytes that are retained within the instrument from previous samples to be released. In this way, depending on the sample matrix, the memory-effected element or analyte may be subject to either a false negative or a false positive signal.

Many chemical elements exhibit notorious memory effect behavior. For example, mercury is retained on the surface of sample introduction devices commonly used for atomic spectroscopy. Typically, a sample is aspirated into a nebulizer which converts the sample into an aerosol. The aerosol is then swept by a gas stream into an excitation source, such as an inductively coupled plasma (ICP) or a flame, where the analytical signal is generated. Mercury is adsorbed onto the walls of the nebulizer and transfer tubing where later, due to its high vapor pressure, it slowly bleeds into the aerosol stream, thereby producing the memory effect described above. Until the mercury has been completely rinsed from the system, samples with low concentrations of mercury cannot be accurately analyzed due to the high background signal. Complete rinsing of the system may take hours.

Many other elements such as arsenic, cadmium, gold, zinc and osmium exhibit memory effects as well. It would be desirable, therefore, to treat an analyte sample to eliminate memory effects for these and other analytes which exhibit a memory effect. Elimination of the memory effect is particularly important for analytical methods such as ICP-spectroscopy which are designed to determine the presence of multiple elements simultaneously. This advantage of ICP spectroscopy instrumentation is lost when mercury and other elements which exhibit a memory effect cannot be determined.

The uniform transport of analytes in an analytical device, is important to accurately to detect an analyte species. Analyte transport efficiency is degraded for analytes having high volatility (high vapor pressure). Such analytes exhibit a memory effect as well as non-uniform transport in the analytical device.

Many methods are known where a particulate reagent is added to an analyte solution. In some methods, the particulate reagent dissolves in the solution during the method. See, for example, DD 219,873 which describes a continuous flow method for determining HF and $FeF_2/FeF_3$ where an aqueous suspension of MgO is added to the sample. The MgO is not insoluble, however, and dissolves in the solution during the method.

In other known methods, the particulate reagent is detected as part of the detection process. Many of these methods are related to immunoassay determinations of specific analytes or antigens. U.S. Pat. No. 4,650,770, for example, describes an immunoassay employing fluorescent particles and adsorbent particles. The adsorbent particles substantially inhibit fluorescence when bound to the fluorescent particles through specific non-covalent binding. The decrease in fluorescence of the insoluble particles is then measured.

DE 2,749,956 describes an immunoassay method using photometric detection of latex polymer reagents. Several measurements are made in this kinetic method which cannot be readily adapted to continuously flowing analyte streams. Japanese patent Nos. 59/171863, 62/002163, 62/093663 and 62/093664 are also directed to kinetic methods.

U.S. Pat. No. 4,665,020 describes a flow cytometric measurement of a binding competition immunoassay where a liquid sample containing analyte is mixed with reagent antigen coated fluorescent microspheres and larger microspheres coated with an antibody which bind specifically with the antigen. The particle suspension is measured using a laser flow cytometer for fluorescence and light scattering to provide data correlating to the analyte concentration in the sample. The particles are measured by fluorescence.

U.S. Pat. Nos. 4,588,680; 4,414,325; 4,503,143; 4,451,434; 4,703,017 and 4,458,014 describe methods of detecting analytes such as viruses, enzymes, microorganisms and other analytes where the analyte is bound to a particle and the analyte is detected by fluorescence or a color change.

U.S. Pat. No. 4,097,338 describes a method for determining a reduced coenzyme where the fluorescence of the reduced coenzyme is measured in an aqueous medium in the simultaneous presence of an organic liquid miscible with water and a dispersion of one or more slightly soluble or insoluble substances. The presence and combination of the organic liquid and particles enhances the fluorescence of the reduced coenzyme.

Canadian patent 1,103,137 discloses titration of an ion exchange colloidal polymer with an oppositely charged colloidal particle.

A surface-enhanced Raman spectroscopy technique for high pressure liquid chromatography (HPLC) and flow injection analysis (FIA) detection is described by Freeman et al, Applied Spectroscopy, 1988, 42:456. Analytes are adsorbed to colloidal silver and then the Raman spectrum is measured.

A reagent having an iron oxide nucleus and two layers of surfactants which can be used to magnetize particles and solid materials in non-aqueous environments is described in R & D Magazine, April 1992, p. 132.

In the methods described above where the particle is part of the detection process. Preconcentration of the particles does not decrease the detection limit because the background signal is also increased upon preconcentration. Processes in which the particular reagent dissolves in the analyte solution do not allow one to preconcentrate the sample. None of these methods allow one to effectively eliminate memory effects.

Ion-exchange resins are well known and extensively used to treat liquids and alter the chemical and physical properties of liquids. General uses of such resins include water softening (DE 1,294,933), pH control (U.S. Pat. No. 2,563,006), etc. carried out using a variety of apparatus, for example, those described in U.S. Pat. Nos. 4,900,434, 4,978,506, FR 1,577,527 and SU 671,828.

Another common use of ion-exchange resins is to chelate and preconcentrate trace elements in a sample for later analysis. A variety of chelating resins used to preconcentrate different analytes are described, for example, Horvath et al, Anal. Chem., 1986, 58:1352–1355; Horvath et al, Anal. Chim. Acta, 1985, 173:305–309; Koster et al, Anal. Chim. Acta, 1967, 38:179–184; Dumont et al, Appl. Spectr., 1989, 43:1132–1135; and Greenfield et al, Anal. Proc., 1989, 26:382–284. Soluble chelating compounds have also been used to extract and effect preliminary separation of analytes such as plutonium as described, for example, in Yu et al, Zhur. Anal. Khim., 1966, 21:1217–1222 (English translation).

Watson et al, S. Afr. J. Chem., 1984, 37:81–84 describes determination of trace noble metals by adsorption onto ion-exchange resin particles followed by direct injection into an ICP source. In this process, a specific ion-exchange resin was ground so as to pass through a 200 mesh screen (maximum grain size of 75 $\mu$m). Platinum, palladium, ruthenium, rhodium and gold analytes contained in leach residues were adsorbed onto the ion-exchange resin. A slurry is then formed from the resin with adsorbed metal analyte, the slurry is fed to a nebulizer and then to an ICP source. This method suffers from several disadvantages. Slurries are not stable suspensions and result in settling of large size particles within minutes. This type of slurry requires constant agitation to maintain the large particles in suspension. Further, use of large size particles to adsorb the analyte metals provides a non-uniform sample matrix for presentation to the ICP source. Use of a non-uniform sample matrix decreases the sensitivity of a detection method.

A need continues to exist, therefore, for improved analytical methods for detecting analytes. A need also exists for improved analytical methods for preconcentrating analytical samples, increasing sensitivity and analytical methods and eliminating memory effects.

SUMMARY OF THE INVENTION

Accordingly, one object of the present invention is to provide an analytical method which overcomes the deficiencies of the prior art.

A further object is to provide an analytical method in which an analytical sample can be preconcentrated while increasing sensitivity of the detection method.

A further object is to provide an analytical method which substantially eliminates memory effects.

These and other objects which will become apparent from the following specification have been achieved by the present analytical method for determining the presence or concentration of an original analyte in a solution sample by mixing the solution sample with a particulate reagent prior to analysis and then detecting the analyte using a detecting means. In the present method, the solution sample is mixed with a particulate reagent to form a flowable suspension where the original analyte becomes bound to the particulate reagent to form an amount of analyte-bound particulate which correlates with the concentration of the original analyte in the sample solution. The analyte-bound particulate is then subjected to analysis to directly detect the analyte bound to the particulate reagent with the detecting means without detecting the presence of the particulate reagent.

DETAILED DESCRIPTION OF THE PREFERRED EMBODIMENTS

Figure 1:
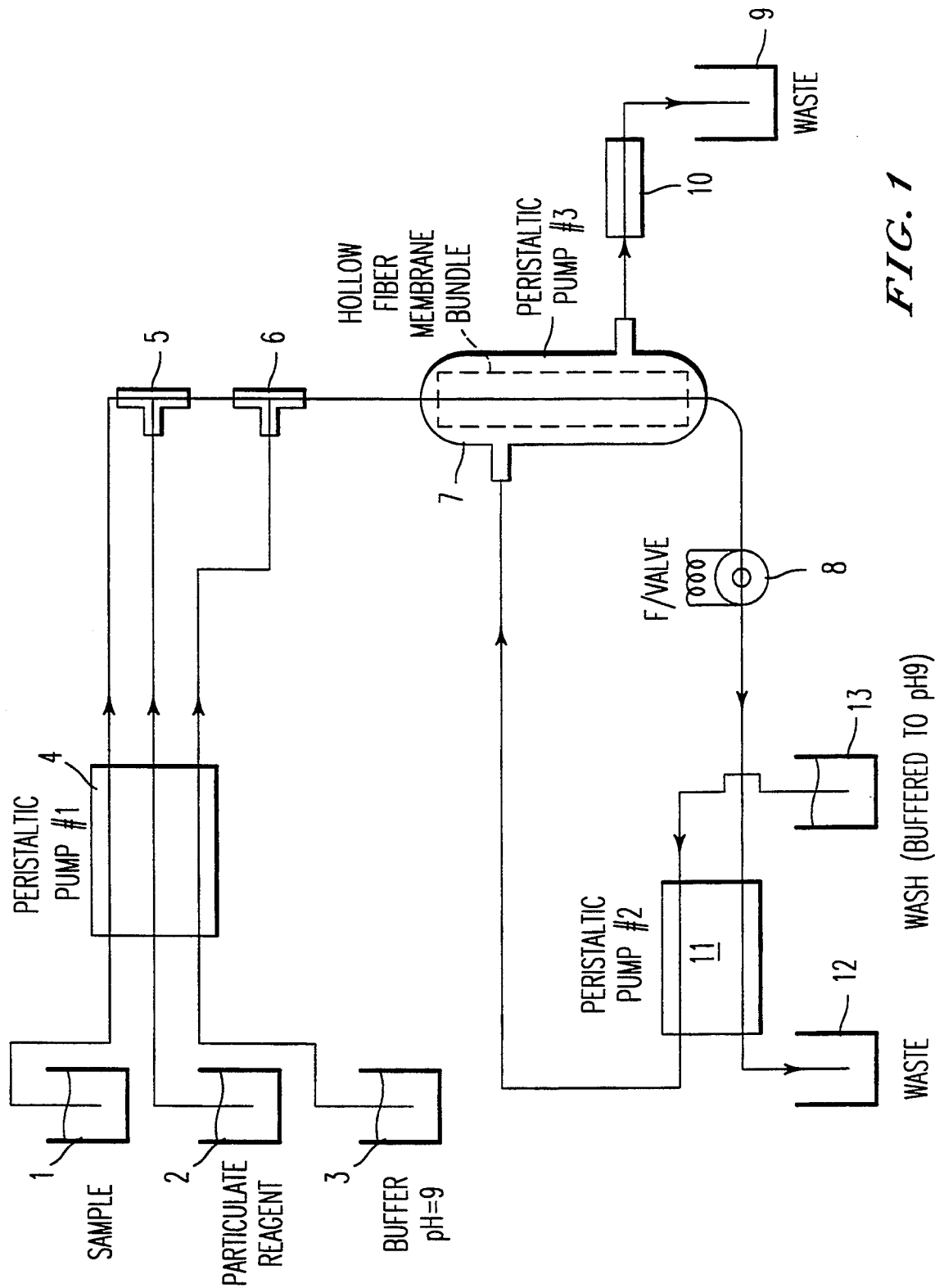
FIG. 1 shows a schematic diagram of an apparatus which may be used to conduct the analytical method of the present invention.

The present invention is an improved analytical method for determining the presence or concentration of an analyte in a sample solution by binding the analyte to a particulate reagent prior to analysis. The improvement of the present method is manifested through the elimination of memory effects by preventing the analyte from being retained on the surface of the analytical instrument or detecting means. In addition, the present method improves detection sensitivity by utilizing a uniform defined sample matrix, uniform transport efficiency, the ability to tailor particulate reagents chemistry to specific analytes, and/or concentration of the analyte. Unwanted matrix components are removed by selective binding of the analyte to the particulate reagent allowing removal of the solvent or solvent matrix from the suspension of the analyte-bound particulate.

Particulate reagents which can be used in the present invention are in the form of a stable, flowable suspension. By "stable, flowable suspension" as used in connection with the present invention, is meant a suspension of small particles which is stable, i.e., particles do not precipitate or settle out from the suspension, over a period of time during which a sample is prepared and analyzed, generally about 2–3 hours. The stability of the suspension of the present invention is independent of the concentration of particles in the suspension. This means that one can add relatively large amounts of solvent, e.g., water, to the stable suspension without causing settling or precipitation of the particles. For example, it is possible to dilute the stable suspension of the present invention by infinite dilution without precipitation of particles. The stable flowable suspension should have a particle/solvent ratio (w/v) of up to about 1/200, preferably from about 1/100,000 to about 1/1000. Preferably, the stable suspension contains particles having a particle diameter up to about 5.0 microns, preferably up to about 2.0 microns. When larger particle sizes are present, the stability of the suspension deteriorates and particles settle rapidly over the course of about 1–2 hours. Such unstable suspensions require continuous agitation to maintain the suspension in contrast to the stable suspensions of the present invention in which no agitation is required and the small particles remain in suspension for long periods of time.

When the method of the present invention is used to eliminate memory effects, the particle size diameters may range up to about 5.0 microns, preferably up to about 2.0 microns with no lower limit. From a practical standpoint, however, the particle size will generally range from about 0.02–5.0 microns. When the method of the present invention is used to preconcentrate an analyte prior to analysis, the particle diameters will generally range from about 0.02–5.0 microns. For preconcentration processes utilizing cross filtration across membranes, it is necessary that the pore size of the membrane be sufficiently small to exclude the particulate reagent. Accordingly, for concentration or preconcentration, the lower limit of the particle size diameter should be larger than the membrane pore size. A lower limit in the range of about 0.02 to about 0.3 microns is preferred.

Individual particle sizes may vary in the particulate reagent so long as substantially all of the particles have a particle diameter less than about 5.0 microns. By "substantially all of the particles" is meant that 95–100%, preferably 98–100% of the particles in the particulate reagent have a diameter of about 5.0 microns or less. In a particularly preferred embodiment, the particle size diameters fall within a narrow diameter range and thereby provide a narrow particle size distribution.

Suitable particulate reagents may incorporate chemical functional groups, such as cation exchange resins, anion exchange resins, reversed phase column chromatographic materials, chelating ion exchange resins, and any other type of particulate reagent which is capable of binding the analyte of interest.

Many substances have the ability to behave as ion-exchangers. These substances include clays, natural and synthetic zeolites, certain glasses, some inorganic oxides and insoluble salts, and some functionalized organic polymers. The most important type of ion-exchange resins are made from organic polymers such as styrene-divinylbenzene copolymers or exchangers where an ion-exchange material is grafted or chemically bonded to a silica substrate. Examples of typical ion-exchangers useable in the present invention are shown below. These materials may be milled to the desired particle size using known methods and equipment.

| | Examples of ion exchange types. | |
|---|---|---|
| Type | Example | Example Formula |
| Clay | kaolinite | $Al_2Si_2O_5(OH)_4$ |
| Zeolite | natrolite | $Na_2(Al_2Si_3O_{10}).2H_2O$ |
| Inorganic Oxide | alumina | $Al_2O_3$ |
| Inorganic Salt | zirconium phosphate | $Zr(HPO_4)_2.H_2O$ |
| Polymer | DOWEX 1X8 | $C_2H_3(C_6H_4)CH_2N(CH_3)_3Cl$ |

Chelating ion-exchange resins have a chelating functional group built into or covalently attached to a polymer resin. Chelating resins are capable of taking up only a small group of metal ions or may complex a larger group of metal ions, where selectivity is obtained through pH control. Typical chelating resins which can be used in the present invention include iminodiacetic acid resins, hydroxyoxime resins, thioglycolate resins, acetamide resins, N-benzoylmethylhydroxylamine resins, isothiuronium resins, and resins containing crown ether groups (e.g., 14-crown-4, 18-crown-6) which take up and chelate alkali and alkaline earth metal ions. Specific resins are commercially available in particulate form in a variety of particle sizes. These resins may be milled to the desired particle size using known methods. Any of these commercially available chelating resins may be used in the present invention.

In addition to ion-exchange and chelating resins, normal phase and reverse phase chromatography materials may be used as the particulate reagent in the present invention. Common normal and reverse phase chromatography materials which may used in the present invention are shown in the table below.

| Type | Support | Trademark Names |
|---|---|---|
| Nonpellicular | Diatomaceous earths<br>Porous silica beads<br>Silica gel | PORASIL |
| Pellicular | Inactive silica | ZIPAX |
| Pellicular, chemically bonded | Octadecyl-silicone/silica<br>Silicone ether/silica<br>Silicate ester/silica | PERMAPHASE ODS,<br>CORASIL ODS<br>PERMAPHASE ETH<br>DURAPAK/CORASIL |
| Pellicular, for adsorption chromatography | Alumina<br>Silica<br>Polyamide | PELLALUMINA<br>CORASIL I and II<br>PELLOSIL, VYDEC<br>PELLIDON |

Additional chelating ion-exchange and ion-exchange resins which can be used as the particulate reagent in the present invention are described in D. T. Gjerde and J. S. Fritz, "Ion Chromatography", Heuthig:Heidelberg, 1987. Additional normal phase and reversed phase chromatography materials which can be used as the particulate reagent of the present invention are described in L. R. Snyder and J. J. Kirkland, "Introduction to Modern Liquid Chromatography", Wiley:New York, 1979. Any of the resins or chromatography materials described in these references may be used in the present invention and milled to the desired particle size.

In the first step of the present method, a sample analyte in the sample solution is bound to the particulate reagent to form a stable flowable suspension. The analyte-bound particulate reagent is in the form of a flowable suspension of small particles which remain in suspension with little or no agitation. Thus, the analyte can remain as a fluid while being bound to the solid particulate reagent particles. The flowable suspension can be treated as a liquid sample, i.e., it can be pumped, aspirated, nebulized, and otherwise treated as a fluid. The flowable suspension nature of the analyte-bound particulate suspension is in direct contrast to column bound particulate treatments in which the particulate reagents are immobilized within a column or slurries containing large particles. The analyte solution is mixed with the particulate reagent to form the flowable suspension of analyte-bound particulate prior to entry of the flowable suspension into the analytical instrument and/or detecting means used to detect the analyte. By complexing or binding the analyte to the particulate reagent prior to contact with surfaces in the analytical instrument or detecting means, the memory effect is eliminated. That is, since the analyte is strongly bound to the particulate reagent, it is not available for binding to the walls and other surfaces of the analytical instrument or detecting means.

Since the present method does not require release of the analyte from the particulate reagent prior to analysis (although release may occur), it is possible to use particulate reagents which strongly bind the analyte such that the analyte remains bound to the particulate reagent throughout preconcentration steps, sample transportation steps and even detecting steps. Particulate reagents which strongly bind the analyte provide the most favorable kinetics and equilibrium constants for preconcentration and matrix removal since the analyte remains selectively and strongly bound to the particulate reagent.

For example, a suspension of high capacity, strongly acidic cationic exchanger resin added to a sample will strongly bind cations in the sample to the ion exchanger particulate suspension. Cations which have the highest charge, such as transition metals, will bind most strongly to the cation exchanger. Monovalent cations which poorly bind to the cation exchange resin, such as sodium and potassium ions, remain in the matrix and can be removed by preconcentration steps. The selectivity of the particulate suspension reagent can be further improved by employing a chelating cation exchange resin and controlling the pH of the contacting solution. Generally, the pH is adjusted to provide maximum chelating efficiency of the chelating exchange resin for a specific analyte.

If the only process desired is the elimination of the memory effect, the amount or concentration of the analyte can be measured directly by introducing the analyte-bound particle suspension into an appropriate instrument or detecting means. Suitable analytical instruments include flame atomic absorption spectrometers or inductively coupled plasma atomic emission spectrometers. In these processes, the flame or plasma destroys the particulate reagent and/or releases the analyte from the particulate reagent so that it can be measured. Any analytical instrument or detecting means which can directly detect the presence or concentration of the analyte bound to the particulate reagent may be used in this process.

By "directly detecting" is meant an analytical method which detects a property of the analyte which is distinct from the properties of the particulate reagent. Directly detecting the analyte, therefore, allows one to detect the presence or concentration of the analyte without detecting the presence of the particulate reagent. Typically, the spectral properties of the analyte, such as the emission spectrum, absorption spectrum, fluorescence spectrum or mass spectrum of the analyte can be detected without detecting the presence of the particulate reagents since the absorption, emission, fluorescence and mass spectral properties of the analyte are distinct and separate from the properties of the particulate reagent. Chemiluminescence can also be used to directly detect the analyte.

An analyte may also be "directly detected", without detecting the presence of the particulate reagent, when the analyte is released from the particulate reagent prior to or during detection. For example, introducing the analyte-bound particulate reagent into a flame, graphite furnace or into an inductively coupled plasma may release the analyte from the particulate reagent. The analyte may then be directly detected using atomic absorption or atomic emission spectroscopy or may be analyzed using a mass spectrometer. When using a mass spectrometer, the unique mass of analyte ions are detected, where these ions are distinct from mass ions produced by the particulate reagent.

In other embodiments of the analytical method of the present invention, sensitivity can be enhanced alone or in combination with elimination of the memory effect as described above. Sample sensitivity is improved through selective binding of the analyte to the particulate reagent, removal of matrix interferences, uniform transport efficiency and preconcentration. The preconcentration steps of the present invention can be performed continuously and on-line, in contrast to prior analytical determinations which require stepwise or batchwise concentration steps.

In the present invention, preconcentration can be conducted by evaporation or by physical separation of the analyte-particulate reagent from the fluid matrix. Physical separations include filtering, centrifugation, coagulation, precipitation, dialysis, etc. and include any physical separation in which the volume of the analyte-bound particulate reagent collected after preconcentration is less than the volume of the sample solution in which the original analyte was present.

Coagulation, centrifugation and precipitation are preferred preconcentration methods if it is desired to concentrate the sample to the smallest possible volume. The highest possible preconcentration factor is achieved using these processes.

Several preferred preconcentration methods are described below. In a one method, a suspension of the particulate reagent is added to the sample, whereupon the particulate reagent binds the analyte in the sample. The analyte-bound particulate reagent/sample is then centrifuged at high speed. For example, when using a 0.2 $\mu$m high-capacity cation exchange resin, a rotational velocity of about 15,000–20,000 rpm is utilized. Finally, the analyte-bound particulate/sample suspension is resuspended in a liquid carrier and introduced into an analytical instrument. This method can be used, for example, to determine trace amounts of metals in urine, e.g., uranium, lead arsenic or mercury. The resuspended sample may be introduced directly into an ICP-coupled emission spectrometer or an ICP-coupled mass spectrometer.

In another embodiment, preconcentration is effected by filtration. The filtration process may be static or continuous. In static preconcentration, the particulate reagent is reacted with the sample to bind the analyte and then the particulate slurry is filtered to form a cake or dense slurry of the analyte-bound particulate reagent. Filtration can be conducted using conventional and commercially available filters having a pore size sufficiently small to preclude passage of the particular reagent. Additionally, on-line filtration and preconcentration can be performed using cross-flow microfiltration techniques.

Cross-flow microfiltration is performed by causing a solution to flow across a membrane surface. Solvent and sample species which are smaller than the membrane pore size will permeate through the membrane as filtrate. Species larger than the membrane pore size will not permeate and are separated and concentrated. On-line filtration can also be performed by using a cartridge filter (for example, ACRODISC LC13, 0.2 $\mu$m, available from Scientific Products, Hayward, Calif.) and then back flushing the analyte-bound particulate reagent into an analytical instrument. These on-line preconcentration processes require much shorter times than other preconcentration methods and are therefore preferred.

A particularly preferred on-line filtration and preconcentration process uses a hollow membrane filter tube to perform the filtration and preconcentration steps. A flowable particulate suspension is pumped into the hollow fiber membrane. The hollow membrane tube may be completely or partially closed to restrict the flow of particulate suspension through the hollow filter tube. The pore size of the filter membrane is sufficiently small to preclude passage of the analyte-particulate reagent from passing through the filter. For example, when utilizing a suspension of 0.2 $\mu$m particles, a hollow fiber membrane having a 0.1 $\mu$m pore size or smaller would be used.

As the sample stream enters the membrane tube, the analyte-bound particulate is retained inside the hollow membrane filter while the solvent and uncomplexed matrix ions pass through the filter to waste. After the entire sample has been pumped through the membrane, the analyte-bound particulate reagent is quantitatively washed from the hollow fiber filter. The wash volume required to quantitatively remove the analyte-bound particulate from the hollow membrane filter is at least 50 times less than the initial sample volume, resulting in analyte preconcentration. Preferably, the wash volume is 100–200 times less than the initial sample volume.

The analyte-bound particulate reagent may then be directly introduced into an analyzer. For example, when using atomic emission spectroscopy, the analyte-bound particulate may be directly nebulized using a conventional ultrasonic nebulizer or direct injection nebulizer (DIN). Using the analyte preconcentration and matrix elimination of the present invention, detection limits can be improved by at least two orders of magnitude.

In a preferred embodiment, the hollow fibers have high porosity (0.5–70%), uniform pore size with a pore diameter smaller than the particulate reagent, e.g., 0.1 micron pore size for a 0.2 micron particulate reagent, and are chemically resistant to sample constituents. The hollow fiber membrane should chemically resist strongly acidic and basic solutions, for example. The membrane should also be resistant to high pressure gradients (>15 psi) and have a suitably long lifetime. Membranes having one or more of the characteristics described above are suitable for a range of samples.

Typical hollow fiber membranes which may be used in the invention include TEFLON, polyvinylidene fluoride (PVDF), polysulfone, polypropylene, nylon, poly(meth)acrylate, polyethylene, etc. The invention is not limited to a particular membrane material, rather any membrane which will function to retain the particulate reagent while allowing unbound ions and solvent to pass through the membrane will be suitable and can be used in the present invention.

The invention will be further described with reference to FIG. 1 which shows a schematic of an analytical system for use with the method of the present invention. In FIG. 1, sample 1 is pumped into a mixing tee 5 using peristaltic pump 4. Similarly, particulate reagent 2 and buffer 3 are pumped to tee 5 and tee 6 using peristaltic pump 4. Sample and particulate reagent are mixed in mixing tee 5. The pH of the sample/particulate reagent mixture can be adjusted using buffer 3 in mixing tee 6 if necessary to obtain the strongest binding of analyte to particulate reagent. The buffer is optional, however, for particulate reagent resins in which strong analyte bonding occurs without buffering. For analyte species such as iron, copper, tin and chromium, it is important to add the particulate reagent prior to adjusting the pH to prevent hydrolysis of these species.

The sample/particulate reagent then passes into a hollow fiber membrane 7. When the membrane exit is closed, for example using a downstream flow injection valve 8, the membrane acts to trap the analyte-bound particulate while solvent and uncomplexed matrix ions permeate through the membrane and are drawn to waste reservoir 9 using peristaltic pump 10.

After the entire sample has passed through the membrane, peristaltic pump 4 is stopped and the hollow fiber membrane is washed or rinsed by activating peristaltic pump 11. The pumping action of peristaltic pump 11 pressurizes the outside of the hollow fiber membrane releasing the analyte-bound particulate from the membrane walls. Flow valve 8 is opened and peristaltic pump 11 then draws the analyte-bound particulate through the outlet of the hollow fiber membrane and into the loop of the flow injection valve. The analyte can be quantitatively removed from the hollow fiber membrane.

The contents of the flow injection loop may then be nebulized or otherwise directly introduced into a detecting means, i.e., spectrometer, capable of directly detecting the presence of the analyte on the particulate reagent or releasing the analyte from the particulate reagent prior to analysis.

In the description above, the hollow fiber preconcentrator is operated in a discontinuous or batchwise mode. However, the hollow fiber preconcentrator may also be operated in a continuous mode by restricting but not stopping flow of the sample through the outlet of the hollow fiber membrane. Typically, the hollow fiber will restrict flow through the fiber such that the ratio of the outlet flow to the inlet flow is in the range of about 1:1 to 1:100. Restricting the outlet flow to one-tenth of the inlet flow provides a preconcentration factor of 10. For example, the inlet flow into the hollow fiber tube is 10 ml/min and the outlet flow is restricted to 1 ml/min, 9 ml/min of matrix ions and fluids are removed from the analyte-bound particulate reagent wherein the concentration of the analyte is increased by a factor of 10.

The method of the present invention provides for uniform transport efficiency in the analytical device (nebulizer) because the analyte species are bound to the solid particles in the particulate reagent and are thus transported through the device at the same rate as the particles. For small sized particles, this transport rate can be high. Since the analyte is bound to the particles, volatility of the analytes does not change from sample to sample as a result of element speciation ($Cr^{+3}$, $Cr^{+6}$, etc.) or sample matrix. Uniform transport efficiency increases the sensitivity of the method.

The method of the present invention provides for a uniform and defined sample matrix by binding the analyte to the particles in the particulate reagent. For example, in graphite furnace atomic adsorption, use of the particulate reagent and method of the present invention eliminates the need for other matrix modifiers, such as expensive poladium. The solid particles provide a uniform matrix for the sample analytes, regardless of salt concentration in the original sample matrix. Unwanted or unbound matrix components can be eliminated by ultrafiltration, centrifugation, etc. This improves sensitivity, accuracy and detection limit.

Other features of the invention will become apparent in the course of the following descriptions of exemplary embodiments which are given for illustration of the invention and are not intended to be limiting thereof.

EXAMPLES

Example 1

On-line preconcentration of analytes using a hollow filter membrane.

A solution containing 1 ppm each of Mn and Sc and 0.04 wt.% of SPR-hydrogen form cation exchange resin (obtained from Sarasep, Inc.) was pumped through a polysulfone hollow fiber membrane having a 0.1 $\mu$m pore size, 0.5 $\mu$m internal diameter (i.d.), 1 m long, obtained from AG Technologies, Needham, Mass., at a flow rate of 14 ml/min. The liquid flow rate through the outlet of the hollow fiber membrane was restricted to 4.2 ml/min. The difference in liquid volume between the inlet flow and outlet flow permeated through the hollow fiber membrane. The Mn and Sc analytes were chemically bound to the particulate reagent (0.2 $\mu$m diameter) and retained within the hollow fiber membrane passing through the restricted outlet. All of the analyte sample solution pumped into the membrane was thus reconcentrated to provide an increase in the analyte concentration by a factor of 3.3.

The preconcentrated analyte-bound particulate reagent was then directly nebulized using an ultrasonic nebulizer (Cetac U5000 AT ultrasonic nebulizer obtained from Cetac Technologies, Omaha, Nebr.) and directly transported into an ICP-atomic emission spectrometer for elemental analysis. The results, as shown in Table 1, indicate that the analytes were concentrated by a factor of about 3.

TABLE I

| | Mn intensity (counts) | Sc intensity (counts) |
| --- | --- | --- |
| Original Solution | 49,000 | 21,000 |
| After Preconcentration (No particulate reagent) | 34,000 | 14,000 |
| No Preconcentration (Particulate reagent added) | 39,000 | 18,000 |

TABLE I-continued

|  | Mn intensity (counts) | Sc intensity (counts) |
|---|---|---|
| After Preconcentration (Particulate reagent added) | 141,000 | 67,000 |

In a similar manner, a 500 ml tap water sample (Omaha, Nebr.) was spiked with 10 ppb lead and preconcentrated. The concentrated sample had a 496 fold increase in lead concentration.

Example 2

Elimination of memory effect for mercury prior to ICP-MS analysis.

A 0.05 wt.% suspension of H-form particulate reagent (SPR cation exchange resin obtained from Sarasep, Inc.) was added to a sample containing 100 ppb of mercury in 2 wt.% nitric acid. After mixing, an aliquot of the sample was introduced into the ICP-MS instrument. The sample was introduced using a Cetac U5000 AT ultrasonic nebulizer with a peristaltic pump. As a control, a sample containing 100 ppb of mercury in 2 wt.% nitric acid was introduced into the ICP-MS instrument without prior mixing with a particulate reagent.

In the control, a memory effect in the form of an elevated background signal was detected for more than 2 hours. In contrast, when the particulate reagent was added to the sample prior to analysis, the rinse out time required to achieve a steady background signal was only 2 minutes.

Example 3

Elimination of memory effect for mercury prior to ICP-AE analysis.

A 0.05 wt.% suspension of a chelating particulate reagent having an iminodiacetic acid functional group (SPR-IDA obtained from Sarasep, Inc.) was added to a sample containing 5 ppm mercury. After mixing, an aliquot of the sample was introduced into the ICP-AE instrument for analysis. As a control, a sample containing 5 ppm mercury was introduced directly into the ICP-AE without prior mixing with the particulate reagent.

Figure 2:
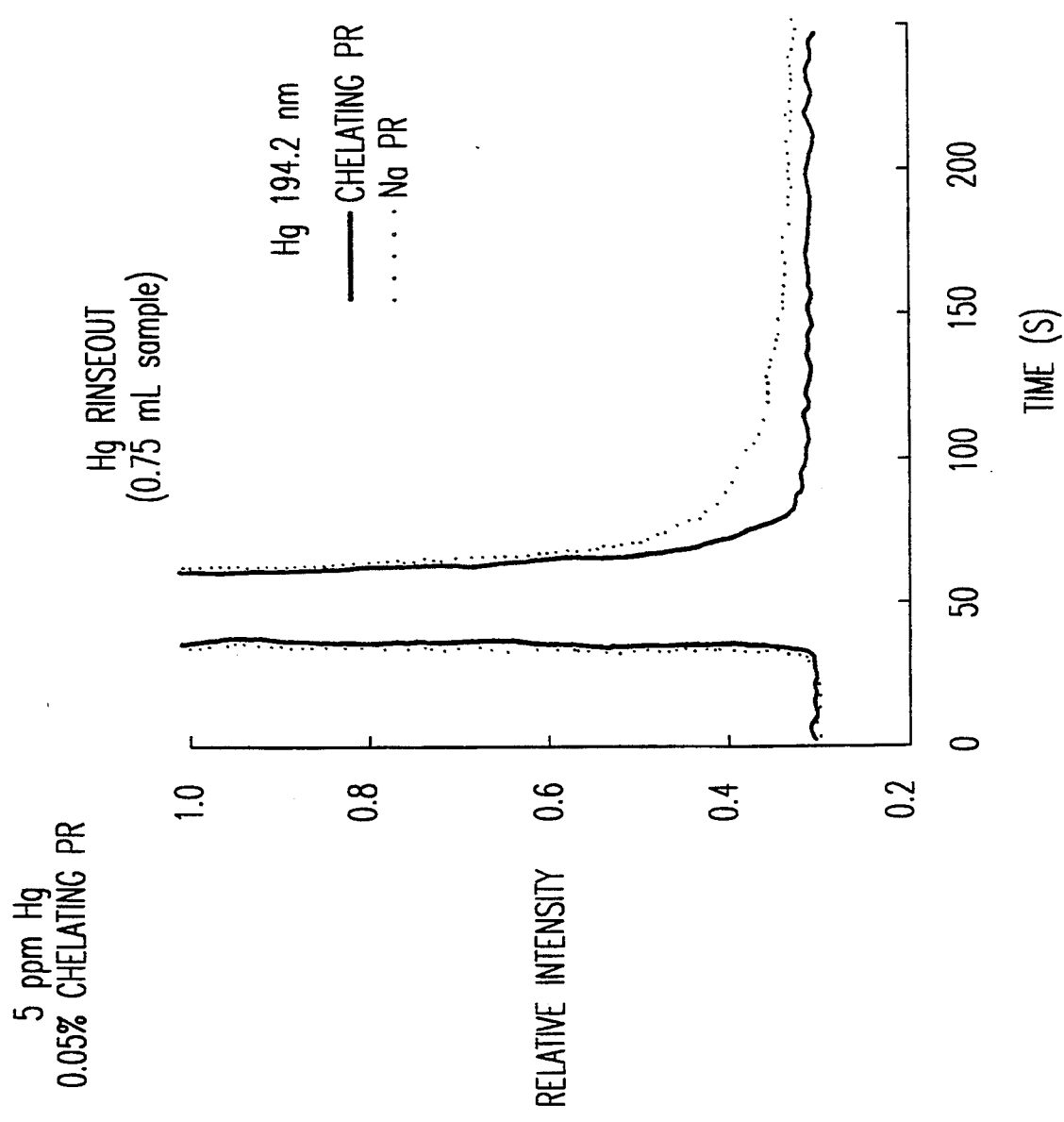
FIG. 2 shows the results of a mercury analysis showing the substantial elimination of the mercury memory effect.

Comparative results are shown in FIG. 2. When using the particulate reagent, the rinse out time necessary to prepare the instrument for the next sample was only 2 minutes. Without premixing with the particulate reagent of the present invention, a bleed background signal corresponding to 40 ppb mercury was observed for up to 1 hour.

Example 4

Uranium and plutonium preconcentration.

A fully sulfonated cation exchange resin in the H-form (2 ml) having average diameter of 0.2 μm (SPR-cation exchange resin obtained from Sarasep, Inc.) was added to an aqueous solution containing 10 ppm uranium (250 ml) to make a final suspension concentration of 0.05M. The sample was filtered and then an anion exchange resin in the OH-form was added in 50% excess. Most of the suspended material precipitated. The remaining material was filtered through a 10 μm filter and the filtrate was then directly analyzed for uranium content by ICP-MS monitoring the $U^{238}$ isotope. The concentration of uranium in the filtrate was 9 parts per trillion, representing an increase in analyte concentration of greater than $10^4$ fold.

Plutonium has a higher selectivity for the sulfonated cation exchange resin and is preconcentrated using the same procedure to obtain an increase in plutonium analyte concentration of greater than $10^4$ fold as well.

Example 5

Elimination of the matrix effect of alkali metal ions.

The levels of matrix elements such as sodium and potassium ions in a sample can be greatly reduced by using a chelating resin having a functionality which does not bind these ions. For example, the imidoacetate (IDA) chelating functional group does not bind alkali metals but will bind transition and rare earth metals. High concentrations of alkali metals are present in many samples, e.g. water samples. Alkali metals can destabilize an ICP, clog some injection systems, and cause severe signal suppression, especially with ICP-mass spectroscopy systems.

An IDA resin (0.001%) was added to a 500 ml sample of Atlantic ocean seawater and the pH was adjusted to 8 with high-purity ammonium hydroxide. All of the sample was pumped at a 10 ml/min. flow rate through a hollow fiber cartridge with the outlet blocked, and the unbound sodium was passed to permeate waste. The IDA resin and any complexed metal cations remained trapped in the pores of the hollow fibers. Pumping about 25 ml of deionized water with a pH of 8 rinsed the cartridge of the residual seawater matrix. The cartridge outlet was then opened with the permeate outlet blocked. The concentrated IDA resin and the complexed metal cations were collected in a 1 ml volume. The level of sodium in the seawater (about 10,000 ppm) was reduced to 5 ppm or less in the concentrated sample.

To confirm recovery of lead with elimination of a sodium matrix, a 10 ppb spike of lead was placed in 500 ml of Omaha tap water. The matrix removal procedure was performed as above with 99-2% recovery of the lead spike.

Example 6

BioRad AG1X10 (<63 μm) anion exchange resin (3 g) was stirred into 15 ml of water at a resin/water (w/v) ratio of 1/5 to give a stable slurry. Adding water to the slurry to produce a 1/25 ratio resulted in the resin particles settling within less that 1 min. The resin beads completely settled out in 2-3 min.

SPR-H cation exchange resin (0.2 μm) was suspended in water at a resin/water ratio of 1/100. The suspension was stable indefinitely. Additional water was added to produce a resin/water ratio of 1/1000. This suspension was also stable (no particles settling) indefinitely.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An analytical method for qualitatively or quantitatively determining the presence of an analyte in a sample with an analytical device, comprising the steps of:
   mixing the sample with a particulate reagent to form a stable flowable suspension, where the analyte is bound to said particulate reagent to form an amount of insoluble analyte-bound particulate which correlates with the amount of analyte in the sample, flowing the stable flowable suspension to a detecting site, and directly detecting the analyte bound to the particulate reagent at said detecting site without detecting the presence of said particulate reagent, wherein the analyte is released from the particulate reagent during said detecting step.

2. The method of claim 1, comprising measuring a spectral property of the analyte.

3. The method of claim 1, comprising measuring the emission, absorption, fluorescence or mass spectrum of the analyte.

4. The method of claim 1, wherein said detecting step comprises introducing the insoluble analyte-bound particulate into an inductively coupled plasma.

5. The method of claim 1, wherein said detecting step comprises introducing the insoluble analyte-bound particulate into a flame or graphite furnace.

6. The method of claim 1, wherein the particulate reagent has a particle size diameter up to about 5 $\mu$m.

7. The method of claim 1, wherein said stable flowable suspension is formed before said stable flowable suspension is introduced into the analytical device.

8. The method of claim 1, further comprising concentrating the amount of particulate reagent in the stable flowable suspension prior to said detecting step.

9. The method of claim 8, comprising concentrating the stable flowable suspension by cross-flow microfiltration.

10. The method of claim 8, comprising concentrating the stable flowable suspension by centrifugation.

11. The method of claim 8, comprising concentrating the stable flowable suspension by precipitation.

12. The method of claim 8, comprising concentrating the stable flowable suspension using a continuous process.

13. The method of claim 8, comprising concentrating the stable flowable suspension using a batchwise process.

14. The method of claim 1, wherein the particulate reagent is destroyed during said detecting step.

15. An analytical method for qualitatively or quantitatively determining the presence of an analyte in a sample with an analytical device, comprising the steps of:

mixing the sample with a particulate reagent to form a stable flowable suspension, where the analyte is bound to said particulate reagent to form an amount of insoluble analyte-bound particulate which correlates with the amount of analyte in the sample, wherein the particulate reagent has a particle size of about 0.02 to 5 $\mu$m, flowing the stable flowable suspension to a detecting site, and directly detecting the analyte bound to the particulate reagents at said detecting site without detecting the presence of said particulate reagent, wherein the analyte is released from the particulate reagent during said detecting step.

16. An analytical method for qualitatively or quantitatively determining the presence of an analyte in a sample by introducing the sample into an analytical device, comprising the steps of:

mixing a sample with a particulate reagent to form a stable flowable suspension before said stable flowable suspension is introduced into the analytical device, wherein the analyte is bound to said particulate reagent to form an amount of insoluble analyte-bound particulate which correlates with the amount of analyte in the sample, introducing the stable flowable suspension into a nebulizer and then into an inductively coupled plasma, and then detecting the analyte by measuring the atomic emission or mass spectrum of the analyte, wherein the analyte is released from the particulate reagent and the particulate reagent is destroyed during said detecting step.

17. An analytical method for qualitatively or quantitatively determining the presence of an analyte in a sample with an analytical device, comprising the steps of:

mixing the sample with a particulate reagent to form a stable flowable suspension, wherein said stable flowable suspension comprises particles and solvent and the particle/solvent ratio is equal to or less than 1/200 and where the analyte is bound to said particulate reagent to form an amount of insoluble analyte-bound particulate which correlates with the amount of analyte in the sample, flowing the stable flowable suspension to a detecting site, and directly detecting the analyte bound to the particulate reagent at said detecting site without detecting the presence of said particulate reagent, wherein the analyte is released from the particulate reagent during said detecting step.

18. The method of claim 17, wherein the particle/solvent ratio is about 1/100,000 to about 1/1000.

19. The method of claim 17, wherein the particulate reagent is destroyed during said detecting step.

20. A method for concentrating an analyte in a solution sample, comprising the steps of:

mixing the solution sample with a particulate reagent to form a stable flowable suspension, wherein the analyte is bound to said particulate reagent to form an insoluble analyte-bound particulate, and concentrating the stable flowable suspension to form a concentrated suspension, wherein the amount of insoluble analyte-bound particulate in the concentrated suspension is proportionally related to the amount of analyte in the sample solution, flowing the stable flowable suspension to a detecting site, and directly detecting the analyte bound to the particulate reagent at said detecting site without detecting the presence of the particulate reagent, wherein the analyte is released from the particulate reagent during said detecting step.

21. The method of claim 20, wherein the stable flowable suspension is concentrated by filtration.

22. The method of claim 20, wherein the stable flowable suspension is concentrated by precipitation.

23. The method of claim 20, wherein said stable flowable suspension comprises particles and solvent and the particle/solvent ratio is equal to or less than 1/200.

24. The method of claim 20, wherein the particulate reagent is destroyed during said detecting step.

25. A method of qualitatively or quantitatively determining the presence of an analyte in a sample by introducing the sample into an analytical device while eliminating the detection of residual analyte from a prior analysis in the analytical device, comprising the steps of:

mixing the sample with a particulate reagent to form a stable flowable suspension, where the analyte is bound to said particulate reagent to form an amount of insoluble analyte-bound particulate which correlates with the amount of analyte in the sample, flowing the stable flowable suspension into the analytical device and to a detecting site, and directly detecting the analyte bound to the particulate reagent at said detecting site without detecting the presence of said particulate reagent wherein the analyte is released from the particulate reagent during said detecting step.

26. The method of claim 25, wherein said stable flowable suspension comprises particles and solvent and the particle/solvent ratio is equal to or less than 1/200.

27. The method of claim 25, the particulate reagent is destroyed during said detecting step.

28. A method of removing a detectable matrix component in a sample, comprising the steps of:

mixing the sample with a particulate reagent to form a stable flowable suspension, where the analyte is bound to said particulate reagent to form an amount of insoluble analyte-bound particulate which correlates with the amount of analyte in the sample and wherein the detectable matrix component is not bound to the particulate reagent, separating the unbound detectable matrix component from the particulate reagent, flowing the insoluble analyte-bound particulate to a detecting site, and directly detecting the analyte bound to the particulate reagent at said detecting site without detecting the presence of said particulate reagent wherein the analyte is released from the particulate reagent during said detecting step.

29. The method of claim 28, wherein said stable flowable suspension comprises particles and solvent and the particle/solvent ratio is equal to or less than 1/200.

30. The method of claim 28, wherein the particulate reagent is destroyed during said detecting step.

* * * * *